United States Patent [19]

Ornstein

[11] Patent Number: 5,527,810
[45] Date of Patent: Jun. 18, 1996

[54] DECAHYDROISOQUINOLINE COMPOUNDS AS EXCITATORY AMINO ACID RECEPTOR ANTAGONISTS

[75] Inventor: Paul L. Ornstein, Indianapolis, Ind.

[73] Assignee: Eli Lilly and Company, Indianapolis, Ind.

[21] Appl. No.: 255,590

[22] Filed: Jun. 8, 1994

Related U.S. Application Data

[62] Division of Ser. No. 972,679, Nov. 6, 1992, Pat. No. 5,356,902.

[51] Int. Cl.$^6$ .......................... A01N 43/42; C07D 217/00
[52] U.S. Cl. ........................ 514/307; 546/144; 546/147
[58] Field of Search ................................ 546/144, 147; 514/307

[56] References Cited

U.S. PATENT DOCUMENTS 4,902,695  2/1990  Ornstein .................................. 514/307
5,356,902  10/1994 Ornstein .................................. 514/307

OTHER PUBLICATIONS

Sheardown et al., "2,3–Dihydroxy–6–nitro–7–sulfamoyl–benzo(F)quinoxaline: A Neuroprotectant for Cerebral Ischemia", *Science,* 247, 571 (1990).
Buchan et al., "Delayed AMPA receptor blockade reduces cerebral infarction induced by focal ischemia", *Neuroreport,* 2, 473 (1991).
LePeillet et al., "The non–NMDA antagonists, NBQX and GYKI 52466, protect against cortical and striatal cell loss following transient global ischaemia in the rat", *Brain Research,* 571, 115 (1992).
Ornstein et al., "Syntheses of 6–Oxodecahydro–isoquinoline–3–carboxylates. Useful Intermediates for the Preparation of Conformationally Defined Excitatory Amino Acid Antagonists", *J. Org. Chem.,* 56, 4388 (1991).
Jacques, Collet, and Willen, "Enantiomers, Racemates and Resolutions", 253–259, *John Wiley and Sons,* N.Y., 1981.
Bullock and Fujisawa, "The Role of Glutamate Antagonists for the Treatment of CNS Injury", *J. Neurotrama,* 9 (Supp. 2), S443 (1992).
Scatton et al., "N–Methyl–D–Aspartate Receptor Antagonists: A Novel Therapeutic Perspective for the Treatment of Ischemic Brain Injury", *Cerebrovascular Dis.,* 1, 121 (1991).
Bullock et al., "Focal Cerebral Ishcemia in the Cat: Pretreatment with a Competitive NMDA Receptor Antagonist, D–CPP–ene", *J. Cerebral Blood Flow and Metabolism,* 10, 668 (1990).
Simon and Shirasho, "N–Methyl–D–Aspartate Antagonist Reduces Stroke Size and Regional Glucose Metabolism", *Annals of Neurology,* 27, 606 (1990).
Madden et al., "Efficacy of LY233053, a competitive glutamate antagonist, in experimental central nervous system ischemia", *J. of Neurosurgery,* 76, 106 (1992).
Schoepp et al., "Neuroprotectant effects of LY274614, a structurally novel systemically active competitive NMDA receptor antagonist", *J. of Neural Transmission,* 85, 131 (1991).
Meldrum, "Excitatory amino acids in epilepsy and potential novel therapies", *Epilepsy Research,* 12, 189 (1992).
Meldrum, "Excitatory Amino Acid Transmitters in Epilepsy", *Epilepsia,* 32 (Supp. 2) S1 (1991).
Chapman and Meldrum, "Excitatory amino acids in epilepsy and novel anti–epileptic drugs", New Antiepileptic Drugs, 39 (1991).
France, Winger, and Woods, "Analgesic, anesthetic, and respiratory effects of the competitive N–methyl–D–aspartate (NMDA) antagonist CGS 19755 in rhesus monkeys", *Brain Research,* 526, 355 (1990).
Murray, Cowan, and Larson, "Neurokinin and NMDA antagonists (but not a kainic acid antagonist) are antinociceptive in the mouse formalin model", *Pain,* 44, 179 (1991).

*Primary Examiner*—C. Warren Ivy
*Assistant Examiner*—Raymond Covington
*Attorney, Agent, or Firm*—Martin A. Hay; James P. Leeds

[57] ABSTRACT

This invention provides novel decahydroisoquinoline compounds which are useful as excitatory amino acid receptor antagonists and in the treatment of neurological disorders. This invention also provides synthetic methods for preparing decahydroisoquinolines.

12 Claims, No Drawings

DECAHYDROISOQUINOLINE COMPOUNDS AS EXCITATORY AMINO ACID RECEPTOR ANTAGONISTS

This application is a division of application Ser. No. 07/972,679, filed Nov. 6, 1992, now U.S. Pat. No. 5,356,902.

BACKGROUND OF THE INVENTION

The role of excitatory amino acids, such as glutamic acid and aspartic acid, as the predominant mediators of excitatory synaptic transmission in the central nervous system has been well established. Watkins and Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. The excitatory amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective antagonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic transmission along excitatory pathways, but also participate in the modification of synaptic connections during development and changes in the efficiency of synaptic transmission throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, perinatal hypoxia, cardiac arrest, hypoglycemic neuronal damage, ocular damage and retinopathy, and idiopathic and drug-induced Parkinson's Disease. Other neurological conditions, that are caused by glutamate dysfunction, require neuromodulation. These other neurological conditions include muscular spasms, migraine headaches, urinary incontinence, psychosis, opiate tolerance and withdrawal, anxiety, emesis, brain edema, chronic pain, convulsions, and tardive dyskinesia. The use of a neuroprotective agent, such as an AMPA or NMDA receptor antagonist, is believed to be useful in treating these disorders and/or reducing the amount of neurological damage associated with these disorders. The excitatory amino acid antagonists are also useful as analgesic agents.

Recent studies have shown that AMPA receptor antagonists are neuroprotective in focal and global ischemia models. The competitive AMPA receptor antagonist NBQX (2,3-dihydroxy-6-nitro-7-sulfamoylbenzo[f]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115 (1992). The noncompetitive AMPA receptor antagonist GKYI 52466 has been shown to be an effective neuroprotective agent in rat global ischemia models. LaPeillet et al., *Brain Research*, 571, 115 (1992).

Recent studies have shown that NMDA receptor antagonists are neuroprotective in animal models of focal cerebral ischemia. Bullock and Fujisawa, *Journal of Neurotrauma*, 9 (supplement 2), S443 (1992); Scatton et al., *Cerebrovascular Disease*, 1, 121 (1991). These studies have shown that the competitive NMDA antagonist D-(−)CPP-ene provided protection in a focal cerebral ischemia model in cats, the competitive NMDA antagonist CGS 19755 provided protection in a focal cerebral ischemia model in rats, and the competitive NMDA antagonist LY233053 provided protection in a CNS ischemia model in rabbits. Bullock et al., *Journal of Cerebral Blood Flow and Metabolism*, 10, 668 (1990); Simon and Shirasho, *Annals of Neurology*, 27, 606 (1990); Madden et al., *Journal of Neurosurgery*, 76, 106 (1992). The non-competitive NMDA antagonist dizocilpine provided protection in models of focal cerebral ischemia in cats and rats. Park et al., *Journal of Cerebral Blood Flow and Metabolism*, 8, 757 (1988); Park et al., *Annals of Neurology*, 24, 543 (1988). The competitive NMDA antagonist LY274614 is neuroprotective in an animal model of Huntington's Disease. Schoepp, et al., *Journal of Neural Transmission [General Section]*, 85, 131 (1991).

Several studies have shown that NMDA antagonists are anticonvulsant agents. Meldrum, *Epilepsy Research*, 12, 189 (1992); Meldrum, *Epilepsia*, 32 (supplement 2), S1 (1991); Chapman and Maidrum, New Antiepileptic Drugs (Epilepsy Research Supplement 3), Elsevier, 39 (1991). For example, the competitive NMDA antagonists D-(−)CPP-ene and CGP 37849 are anticonvulsant against sound induced seizures in DBA/2 mice. Chapman, Graham, and Meldrum, *European Journal of Pharmacology*, 178, 97 (1990). Other studies have shown that NMDA antagonists are analgesics. For example, the competitive NMDA antagonist CGS 19755 is analgesic in a warm water tail withdrawal procedure in rhesus monkeys and the competitive NMDA antagonist DL-AP5 was analgesic in a mouse formalin model. France, Winger, and Woods, *Brain Research*, 526, 355 (1990); Murray, Cowan, and Larson, *Pain*, 44, 179 (1991).

These studies strongly suggest that the delayed neuronal degeneration in brain ischemia involves glutamate excitotoxicity mediated at least in part by AMPA and/or NMDA receptor activation. Thus, AMPA and NMDA receptor antagonists may prove useful as neuroprotective agents and improve the neurological outcome of cerebral ischemia in humans.

SUMMARY OF THE INVENTION

The present invention provides compounds which are antagonists of the excitatory amino acid receptors. More specifically, the present invention relates to compounds that are antagonists of the AMPA and NMDA receptors. The present invention relates to a compound of the formula

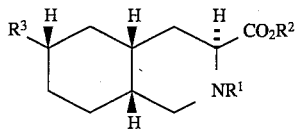

wherein:

$R^1$ is hydrogen, $C_1$–$C_{10}$ alkyl, arylalkyl, alkoxycarbonyl, aryloxycarbonyl or acyl;

$R^2$ is hydrogen, $C_1$–$C_6$ alkyl, substituted alkyl, cycloalkyl, or arylalkyl;

$R^3$ is a group of the formula

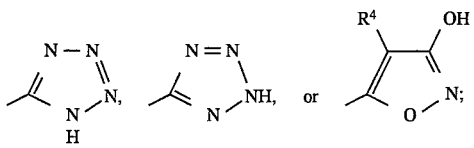

$R^4$ is hydrogen, $C_1$–$C_4$ alkyl, $CF_3$, phenyl, bromo, iodo, or chloro;

or a pharmaceutically acceptable salt thereof.

The invention also provides pharmaceutical formulations comprising a compound of formula I and a pharmaceutically-acceptable carrier, diluent, or excipient.

Further embodiments of the invention include a method of blocking the AMPA or the NMDA excitatory amino acid receptor, as well as methods of treating a neurological disorder which has been linked to these excitatory amino acid receptors, which comprises administering a compound of formula I. Examples of such neurological disorders which are treated with a formula I compound include cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug-induced Parkinson's Disease, anxiety, emesis, brain edema, chronic pain, or tardive dyskinesia. The formula I compounds are also useful as analgesic agents.

DETAILED DESCRIPTION OF THE INVENTION

In the above formula, the term "$C_1$–$C_{10}$ alkyl" represents a straight or branched alkyl chain having from one to ten carbon atoms. Typical $C_1$–$C_{10}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl, and the like. The term "$C_1$–$C_{10}$ alkyl" includes within it the terms "$C_1$–$C_6$ alkyl" and "$C_1$–$C_4$ alkyl". Typical $C_1$–$C_6$ alkyl groups include methyl, ethyl, n-propyl, isopropyl, n-butyl, isobutyl, sec-butyl, t-butyl, n-pentyl, isopentyl, and n-hexyl. Typical $C_1$–$C_4$ alkyl groups include methyl, ethyl, n-propyl, isopropyl, n-butyl, isobutyl, sec-butyl, and t-butyl.

The term "acyl" represents a hydrogen or $C_1$–$C_6$ alkyl group attached to a carbonyl group. Typical acyl groups include formyl, acetyl, propionyl, butyryl, valeryl, and caproyl.

The term "substituted alkyl," as used herein, represents a $C_1$–$C_6$ alkyl group that is substituted by one or more of the following: hydroxy, fluoro, chloro, bromo, and iodo. Examples of a substituted alkyl group include hydroxymethyl, chloromethyl, bromomethyl, iodomethyl, dichloromethyl, dibromomethyl, trichloromethyl, trifluoromethyl, chloroethyl, bromoethyl, perfluoroethyl, 2,2,2-trifluoro-1,1-dichloroethyl, 5-hydroxypentyl, 2-hydroxy-3,3,3-trifluoropropyl, and the like.

The term "$C_1$–$C_4$ alkoxy" represents groups such as methoxy, ethoxy, n-propoxy, isopropoxy, n-butoxy, t-butoxy, and like groups. The term "halogen" refers to the fluoro, chloro, bromo, or iodo groups.

The term "substituted phenyl," as used herein, represents a phenyl group substituted with one or two moieties chosen from the group consisting of halogen, hydroxy, cyano, nitro, $C_1$–$C_6$ alkyl, $C_1$–$C_4$ alkoxy, alkoxycarbonyl, protected carboxy, carboxymethyl, hydroxymethyl, amino, aminomethyl, and trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 4-cyanophenyl, 4-methylphenyl, 3,4-dimethylphenyl, 4-ethylphenyl, 4-methoxyphenyl, 4-carboxyphenyl, 4-(hydroxymethyl)phenyl, 4-aminophenyl, 4-(methoxycarbonyl)phenyl, 4-(protected carboxy)phenyl, 4-trifluoromethylphenyl, and the like.

The term "aryl" represents groups such as phenyl and substituted phenyl as described above. The term "arylalkyl" represents a $C_1$–$C_4$ alkyl group bearing an aryl group. Representatives of this latter group include benzyl, 1-phenylethyl, 2-phenylethyl, 3-phenylpropyl, 4-phenylbutyl, 2-methyl-2-phenylpropyl, (4-chlorophenyl)methyl, (2,6-dichlorophenyl)methyl, (4-hydroxyphenyl)methyl, (2,4-dinitrophenyl)methyl, and the like.

The term "cycloalkyl" represents a $C_3$–$C_7$ cyclic alkyl group such as cyclopropyl, cyclobutyl, cyclopentyl, cyclohexyl, and the like.

The term "alkoxycarbonyl" means a carboxyl group having a $C_1$–$C_6$ alkyl group attached to the carbonyl carbon through an oxygen atom. Representatives of this group include t-butoxycarbonyl and methoxycarbonyl.

The term "aryloxycarbonyl" represents a carboxyl group bearing an aryl group attached to the carbonyl carbon through an oxygen atom. Representatives of this group include phenoxycarbonyl, (4-chlorophenoxy)carbonyl, and (3-nitrophenoxy)carbonyl.

While all the formula I compounds of the present invention are believed to be antagonists of the AMPA and the NMDA excitatory amino acid receptors, certain compounds of the invention are preferred for such use. Preferably, $R^1$ is hydrogen or alkoxycarbonyl; $R^2$ is hydrogen or $C_1$–$C_6$ alkyl; $R^3$ is a group of the formula,

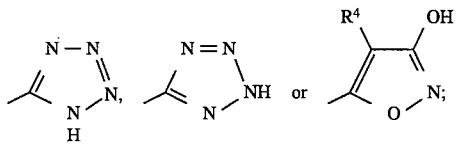

and $R^4$ is hydrogen, $C_1$–$C_4$ alkyl, $CF_3$, or phenyl. Representative compounds from this preferred group of compounds include: 6-(1(2)H-tetrazole-5-yl)decahydroisoquinoline-3-carboxylic acid, ethyl 6-(1(2)H-tetrazole-5

-yl)decahydroisoquinoline-3-carboxylate, 2-methoxycarbonyl- 6-(1(2)H-tetrazole-5-yl)decahydroisoquinoline-3-carboxylic acid, ethyl 2-methoxycarbonyl-6-(1(2)H-tetrazole-5 -yl)decahydroisoquinoline-3-carboxylate, 6-(3 -hydroxyisoxazole-5-yl)decahydroisoquinoline-3-carboxylic acid, ethyl 6-(3-hydroxyisoxazole-5-yl)decahydroisoquinoline-3-carboxylate, 2-methoxycarbonyl-6-(3-hydroxyisoxazole-5 -yl)decahydroisoquinoline-3-carboxylic acid, ethyl 2 -methoxycarbonyl-6-(3-hydroxyisoxazole-5 -yl)decahydroisoquinoline-3-carboxylate, 6-(3-hydroxy-4-methylisoxazole-5-yl)decahydroisoquinoline-3-carboxylic acid, 6-(3-hydroxy- 4-trifluoromethylisoxazole-5-yl)decahydroisoquinoline-3 -carboxylic acid, 6-(3-hydroxy-4-phenyl-isoxazole-5 -yl)decahydroisoquinoline-3-carboxylic acid, and the like.

Certain compounds of the present invention are more preferred for use as antagonists of the AMPA and the NMDA excitatory amino acid receptors. More preferably, $R^1$ is hydrogen or alkoxycarbonyl; $R^2$ is hydrogen or $C_1$–$C_6$ alkyl; and $R^3$ is a group of the formula:

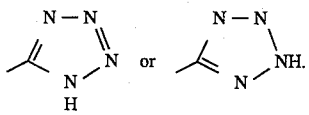

Representative compounds from this more preferred group of compounds include: 6-(1(2)H-tetrazole-5 -yl)decahydroisoquinoline-3-carboxylic acid, ethyl 6-(1(2)H-tetrazole-5 -yl)decahydroisoquinoline-3-carboxylate, 2 -methoxycarbonyl-6-(1(2)H-tetrazole-5-yl)decahydroisoquinoline-3-carboxylic acid, ethyl 2-methoxycarbonyl-6-(1(2)H-tetrazole-5 -yl)decahydroisoquinoline-3-carboxylate, and the like.

Certain compounds of the invention are most preferred for use as antagonists of the AMPA and the NMDA excitatory amino acid receptors. Most preferably, $R^1$ and $R^2$ are hydrogen, and $R^3$ is a group of the formula

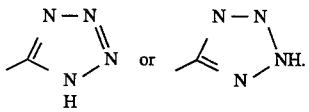

The compound from this most preferred group is (3S, 4aR, 6S, 8aR)-6-(1(2)H-tetrazole-5 -yl)decahydroisoquinoline-3-carboxylic acid.

The formula I compounds of the present invention have the relative stereochemistry shown below:

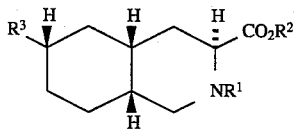

I

The compounds of the present invention possess at least four asymmetric carbon atoms. The asymmetric centers are the substituted carbon atom adjacent to the ring $NR^1$ group (3), the carbon atom where $R^3$ is attached to the ring (6), and the two bridgehead carbon atoms (4a and 8a). As such, the compounds can exist as diastereomers, each of which can exist as the racemic mixture of enantiomers. The compounds of the present invention include not only the racemates, but also the respective enantiomers. The configuration for the diastereomer is 3SR, 4aRS, 6SR, 8aRS, and the configuration for the enantiomer is 3S, 4aR, 6S, 8aR. The relative and absolute stereochemistry for this enantiomer is shown in the following formula.

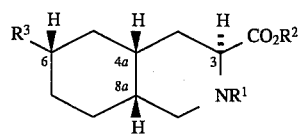

The compounds of the present invention may contain a tetrazole ring, which is known to exist as tautomeric structures. The tetrazole, having the double bond on the nitrogen atom at the 1-position and the hydrogen on the nitrogen atom at the 2-position is named as a 2H tetrazole and is represented by the following structure.

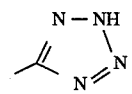

The corresponding tautomeric form wherein the hydrogen is at the nitrogen atom at the 1-position and the double bond on the nitrogen atom at the 4-position is named as a 1H-tetrazole. The 1H-tetrazole is represented by the following formula.

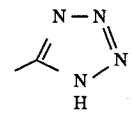

Mixtures of the two tautomers are referred to herein as 1(2)H-tetrazoles. The present invention contemplates both tautomeric forms as well as the combination of the two tautomers.

The present invention includes the pharmaceutically acceptable salts of the compounds defined by formula I. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I, wherein $R^1$ is hydrogen, $C_1$–$C_{10}$ alkyl, or arylalkyl. The alkali metal and alkaline earth metal salts are generally prepared by the reaction of the hydroxide form of the desired metal salt with a compound of formula I, wherein $R^2$ is hydrogen.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, furmarate, hippurate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, napthalene-2-sulfonate, mandelate, ammonium, magnesium, tetramethylammonium, potassium, trimethylammonium, sodium, methylammonium, calcium, and the like salts.

The formula I compounds of the present invention may be chemically synthesized from a common intermediate, 6-oxodecahydroisoquinoline-3-carboxylate (VIII). A synthesis of this compound was described in U.S. Pat. No. 4,902,695, which is incorporated herein by reference. An improved synthesis of this intermediate from d,l-m-tyrosine is shown in Scheme I.

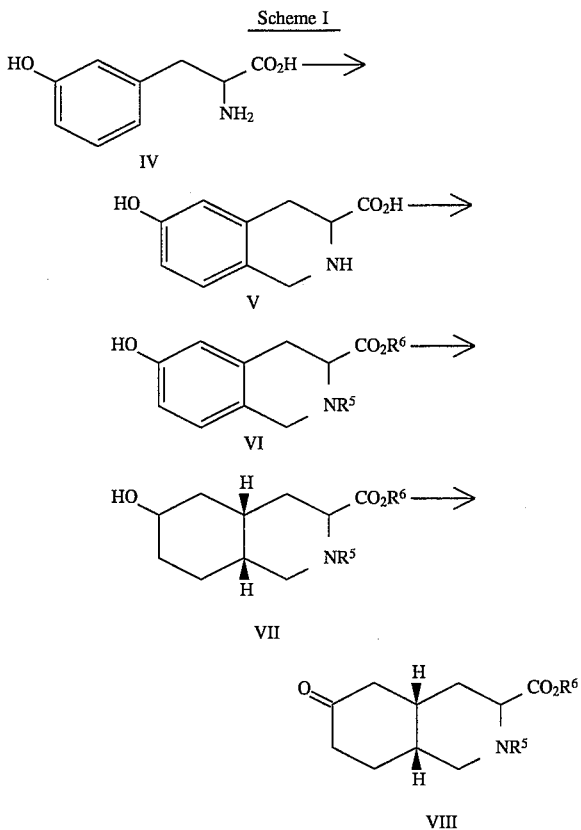

Scheme I

Generally, m-tyrosine (IV) is condensed with formaldehyde to form a 6-hydroxy substituted tetrahydroisoquinoline-3-carboxylic acid (V). This compound is esterified at the carboxyl group and blocked on the ring nitrogen with a suitable protecting group, to provide a doubly protected intermediate (VI). This intermediate is reduced to prepare the protected 6-hydroxydecahydroisoquinoline-3-carboxylate (VII). The 6-hydroxyl group is then oxidized to a 6-oxo group to give common intermediate VIII.

More specifically, meta-tyrosine, preferably racemic m-tyrosine, is condensed with formaldehyde to form the hydroxy substituted tetrahydroisoquinoline-3-carboxylate (V). This reaction is preferably carried out in deionized water containing concentrated hydrochloric acid at a temperature of about 55° C. to about 70° C. for about 0.5 to about 2 hours. The formula V compound is preferably isolated by cooling the reaction mixture to a temperature of about 3° C. to about 10° C. and removing the product by filtration.

This compound is preferably protected on both the 3-carboxyl group and the ring nitrogen. Methods for the protection of amino groups and carboxyl groups are generally described in McOmie, Protective Groups in Organic Chemistry, Plenum Press, N.Y., 1973, and Greene and Wutz, Protecting Groups in Organic Synthesis, 2d. ed., John Wiley and Sons, N.Y., 1991. The carboxyl group may be protected as the $C_1$–$C_6$ alkyl, substituted alkyl, or aryl ester. The preferred ester is the $C_1$–$C_6$ alkyl ester; the ethyl ester is the most preferred. This ester is prepared by the reaction of intermediate V with a mixture of ethanol and concentrated sulfuric acid. The reaction is preferably carried out at the reflux temperature of the solvent for a period of about 16 hours. The ring nitrogen may be protected with an acyl or alkoxycarbonyl group. The preferred protecting groups are t-butoxycarbonyl and methoxycarbonyl. The most preferred protecting group is methoxycarbonyl.

The 2-methoxycarbonyl protecting group is added using standard synthetic organic techniques. The ethyl ester of intermediate V is reacted with methyl chloroformate in the presence of potassium carbonate to form intermediate VI. This reaction is preferably carried out at a temperature of about 0° C. to about 15° C. for a period of about 2 hours. Also, the reaction is preferably carried out by the subsequent addition of potassium carbonate and methyl chloroformate to the esterification reaction mixture. Intermediate VI, wherein $R^5$ is methoxycarbonyl and $R^6$ is ethyl, is preferably isolated by extraction and crystallization (ethanol/water).

Intermediate VII is prepared by reduction of intermediate VI. The preferred method of reduction is catalytic hydrogenation. Suitable catalysts include palladium on carbon, platinum on carbon, palladium on alumina, platinum oxide, ruthenium on alumina, rhodium on alumina, or rhodium on carbon. The preferred catalysts are ruthenium on alumina, rhodium on alumina, or rhodium on carbon. The most preferred catalyst for this reduction is rhodium on carbon. Suitable solvents for the reaction include polar organic solvents, such as ethyl acetate, methanol, and ethanol. Ethyl acetate is the preferred solvent for the reaction. The reduction is carried out at a hydrogen pressure of about 100 psi to about 1000 psi and at a temperature of about 80° C. to about 150° C. When the reaction employs rhodium on alumina, the reaction is complete after about 24 hours. The catalyst may be removed by filtration and the protected 6-hydroxydecahydroisoquinoline-3-carboxylate used in the next step without isolation.

The 6-hydroxy group of intermediate VII is oxidized to a 6-oxo group in the preparation of intermediate VIII. This transformation is preferably accomplished by the use of a mild oxidizing agent. Suitable mild oxidizing agents include sodium hypochlorite, ruthenium trichloride/sodium periodate, and ruthenium trichloride/periodic acid. Other oxidizing agents, such as pyridinium chlorochromate (PCC), Jones' reagent, dimethylsulfoxide/N-chlorosuccinimide, tetrapropylammonium perruthenate (TPAP), pyridine/$SO_3$, and hypochlorous acid, are also useful in effecting this transformation. Preferably, the filtered ethyl acetate solution containing intermediate VII is treated with ruthenium trichloride and water, and the resulting mixture cooled to a temperature of about −10° C. to about 25° C. The two-phase mixture is next treated with periodic acid. After the addition of periodic acid, the reaction mixture is allowed to warm to a temperature of about 20° C. to about 35° C. The desired product, intermediate VIII, is isolated using standard techniques.

Alternatively, intermediate VI is reduced to prepare intermediate VIII. The preferred method of reduction is catalytic hydrogenation. This reaction gives a mixture of 6-hydroxy intermediate VII and 6-keto intermediate VIII. Without further purification, this mixture can be used in a second step to oxidize the 6-hydroxy intermediate VII of the mixture to intermediate VIII using the reagents described in the previous paragraph. Suitable catalysts for the reduction step of this transformation include palladium on carbon and rhodium on carbon. The preferred catalyst is rhodium on carbon. Suitable solvents for this reaction include polar organic solvents, such as ethyl acetate, methanol, and ethanol. Ethyl acetate is a preferred solvent for the reaction. The reduction is carried out at a hydrogen pressure of about 30 psi to about 200 psi and at a temperature of about 70° C. to about 90° C. The preferred conditions for this transformation are a hydrogen pressure of about 100 psi and a temperature of about 85° C. When the reaction employs rhodium on carbon, the reaction is complete after about 2 hours to about 24 hours. The catalyst may be removed by filtration and the products used in the next step without further isolation.

The synthetic scheme described in the preceding paragraphs produces a mixture of diastereomers, whose relative configurations are illustrated by VIIIa and VIIIb.

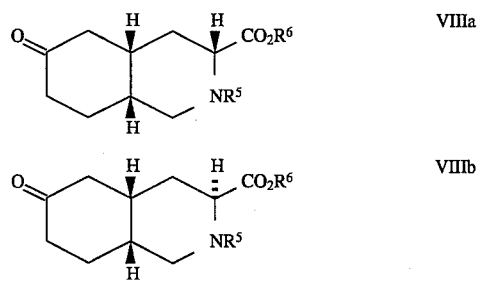

The predominant diastereomer from this scheme is intermediate VIIIa. This mixture of diastereomers may be equilibrated to a mixture where VIIIb is the predominant diastereomer by treatment with a strong base. Suitable strong bases for this equilibration include metal alkoxides, such as sodium ethoxide and potassium t-butoxide, and lithium diisopropylamide. The preferred strong base for the equilibration is sodium ethoxide. When a metal alkoxide is used as a base, the corresponding alcohol may be used as a solvent. The preferred solvent for the equilibration is ethanol. When sodium ethoxide and ethanol are used, the equilibration may be carried out at a temperature of about room temperature to about the reflux temperature of the solvent. Preferably, the equilibration, when carried out in NaOEt/EtOH, is carried out at about 40° C. This equilibration requires from about one to about six hours. The preferred diastereomer, intermediate VIIIb, is isolated by crystallization from ether ($R^5$ is methoxycarbonyl and $R^6$ is ethyl).

The enantiomers of each diastereomeric pair of intermediate VIII are resolved using standard resolution techniques. See Jacques, Collet, and Wilen, Enantiomers, Racemates, and Resolutions, John Wiley and Sons, N.Y., 1981. The preferred method for resolution of the diastereomers and enantiomers uses chiral amines to form the diastereomeric salts. Suitable chiral amines are described in Jacques et al., Chapter 5, pages 253–259. Examples of suitable chiral amines include R-(+)-α-methylbenzylamine, S-(–)-α-methylbenzylamine, (–)-α-(2-naphthyl)ethylamine, yohimbine, (+)-amphetamine, (–)-ephedrine, strychnine, brucine, quinine, quinidine, cinchonine, cinchonidine, and the like. The preferred chiral amines are α-methylbenzylamine, brucine, quinine, quinidine, cinchonine, cinchonidine. The more preferred chiral amines are α-methylbenzylamine, brucine, and quinine. The most preferred chiral amine for the resolution of VIIIb is α-methylbenzylamine.

The preferred method of resolving the preferred enantiomer is described in the following. The ethyl ester, intermediate VIIIb where $R^5$ is methoxycarbonyl and $R^6$ is ethyl, is hydrolyzed using 5N sodium hydroxide at a temperature of about 25° C. to about 40° C. for a period of about 0.5 to about 2 hours. Suitable solvents for this transformation include the alcohols, such as methanol and ethanol. The free acid may be isolated by extraction with ethyl acetate. The free acid, preferably in ethyl acetate solution, is treated with R-(+)-α-methylbenzylamine at a temperature of about 25° C. to about 35° C. for a period of about 15 to about 60 minutes. Intermediate (–)-VIIIb ($R^6$ is hydrogen) precipitates from the reaction solution as the R-(+)-α-methylbenzylamine salt. The material is further purified by reslurrying in warm (45°–50° C.) ethyl acetate. In a similar manner, (+)-VIIIb is prepared using S-(–)-α-methylbenzylamine. The relative and absolute stereochemistry of the structures of these intermediates is shown below. Intermediate (–)-VIIIb is the preferred enantiomer.

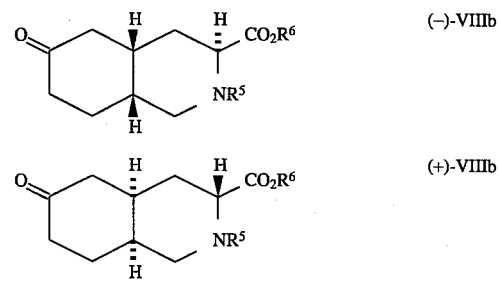

The resolved enantiomer is esterified on the 3-carboxyl group for further chemical modification. The preferred ester is the ethyl ester. Suitable esterification conditions include the reaction of intermediate VIII ($R^6$ is hydrogen) with an akylating reagent in the presence of a base. Suitable akylating reagents for the present transformation include ethyl iodide, ethyl bromide, ethyl chloride, and diethyl sulfate. The base is selected from the group consisting of triethylamine, N,N-diisopropylethylamine, pyridine, collidine, sodium bicarbonate, and sodium carbonate. Suitable solvents for the esterification are polar organic solvents, such as dimethylformamide and acetonitrile. This esterification is preferably carried out using ethyl bromide and triethylamine in acetonitrile at the reflux temperature of the solvent for a period of about one to two hours.

The compounds of the present invention are chemically synthesized from common intermediate VIII by a number of different routes. When the synthesis begins with racemic intermediate VIII, the products are generally racemic mixtures. However, when the synthesis begins with intermediate (–)-VIIIb, the product is a single enantiomer. The specific synthetic steps of the routes described herein may be combined in other ways to prepare the formula I compounds. The following discussion is not intended to be limiting to the scope of the present invention, and should not be so construed.

The formula I compounds wherein $R^B$ is a tetrazole group are prepared as outlined in Scheme II.

Scheme II

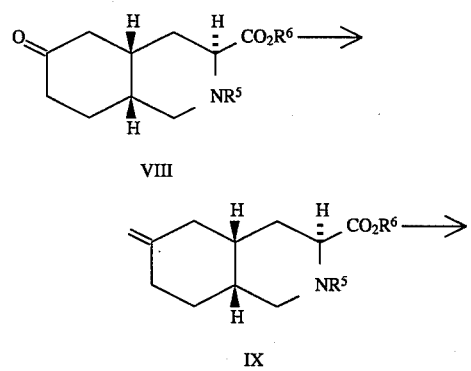

Scheme II -continued

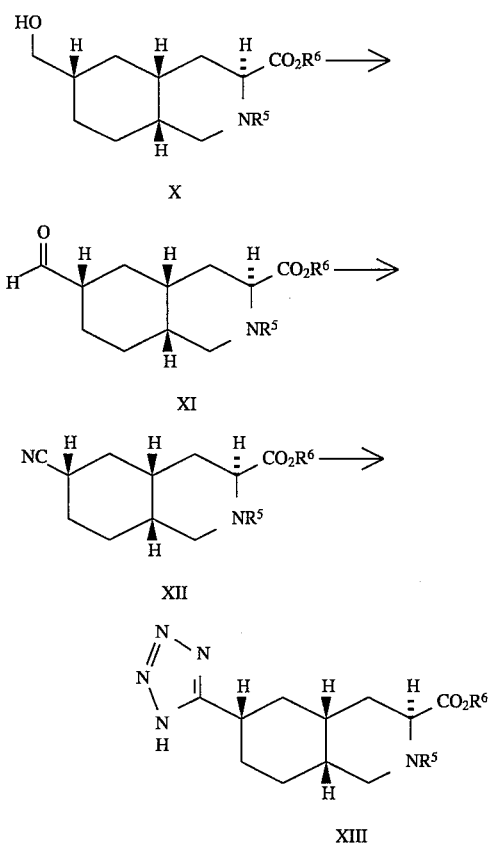

Generally, intermediate VIII is reacted with a Witrig reagent to prepare unsaturated intermediate IX. This intermediate is stereoselectively converted to intermediate X by hydroboration and then oxidation. Hydroxymethyl intermediate X is then oxidized to 6-formyl intermediate XI. The 6-formyl group is then converted to a nitrile through an intermediate oxime. The 6-cyano intermediate XII is then converted to a formula I compound wherein $R^3$ is a tetrazole group.

More specifically, intermediate VIII is reacted with a Wittig reagent, such as methyltriphenylphosphonium bromide, to produce intermediate IX. This reaction is generally accomplished by treating the phosphonium salt with a strong base, such as bis(trimethylsilyl)amide, to generate an ylid. This ylid is then reacted in a polar organic solvent, such as dry tetrahydrofuran, with VIII to provide the unsaturated intermediate IX. This reaction is generally carried out at a temperature of about −10° C. to about 10° C., preferably at 0° C. When a slight molar excess of phosphonium salt is employed, the reaction is generally complete in about one hour.

Intermediate IX is then converted stereoselectively to intermediate X. The preferred method of accomplishing this conversion is hydroboration followed by oxidation. A suitable reagent for the hydroboration is borane-methyl sulfide. This hydroboration is generally carried out in a polar organic solvent, such as tetrahydrofuran, at a temperature of about −10° C. to about room temperature, preferably at about 0° C. The reaction is generally complete after a period of about 2 to about 4 hours. The product from the hydroboration is then oxidized to intermediate X. A suitable oxidizing agent for this transformation is hydrogen peroxide. The oxidation is generally accomplished by treating the hydroboration reaction mixture with hydrogen peroxide and base, such as sodium hydroxide, and stirring the resulting mixture at a temperature of about 0° C. to about room temperature, preferably at room temperature. The reaction is generally complete after a period of about one to about two hours.

The hydroxy intermediate X is then converted to aldehyde intermediate XI. The hydroxyl group is oxidized to the aldehyde with oxidizing reagents and methods which are well known in the chemical arts, such as the Swern oxidant or other dimethylsulfoxide (DMSO) based reagents. Mancuso, Huang, and Swern, *J. Org. Chem.*, 43, 2480–2482 (1978); Epstein and Sweat, *Chem. Rev.*, 67, 247–260 (1967); and Smith, Leenay, Lin, Nelson, and Ball, *Tetr. Lett.*, 29, 49–52 (1988). One such reagent is a combination of oxalyl chloride and dimethylsulfoxide. Generally, dimethylsulfoxide (DMSO) and oxalyl chloride are combined in an organic solvent, such as methylene chloride, at about −78° C. to form the oxidizing agent. After about five to about fifteen minutes, a solution of the alcohol intermediate is added to the cold oxidizing agent solution. To prevent racemization of the C-6 hydrogen, this mixture is then treated with N,N-diisopropylethylamine (Hunig's base), and the resulting reaction mixture cooled to about −78° C. to about −50° C. The reaction is quenched by the addition of a saturated ammonium chloride solution.

Intermediate XI is then converted to intermediate XII. A preferred method of accomplishing this conversion is formation of the corresponding oxime followed by dehydration. A suitable reagent for the oximation is hydroxylamine hydrochloride. This oximation is generally carried out in a polar organic solvent, such as methanol, ethanol, or methylene chloride, or a mixture of polar organic solvents, such as a mixture of methylene chloride and methanol. The reaction is also carried out in the presence of an amine base, such as pyridine, N,N-diisopropylethylamine, triethylamine, N-methylmorpholine, or collidine. This oximation is also generally carried out at a temperature of about 25° C. to about the reflux temperature of the solvent, preferably at room temperature. The reaction is generally complete after a period of about 30 minutes to about 2 hours. The product from oximation is then dehydrated to intermediate XII. A suitable dehydrating agent for this transformation is phenylphosphonic dichloride, tosyl chloride, mesyl chloride, and phosphorous oxychloride. The dehydration is generally accomplished by treating the oxime with the dehydrating agent in the presence of an amine base. This dehydration is generally carried out in a polar organic solvent, such as methylene chloride, at a temperature of about 0° C. to about room temperature, preferably at 0° C. The reaction is generally complete after a period of about 18 to about 24 hours.

Intermediate XII is converted to tetrazole intermediate XIII by treatment with tributyltin azide. The nitrile intermediate is reacted with tributyltin azide at a temperature of about 50° C. to about 120° C., preferably at a temperature of about 80° C. The reaction is generally complete after a period of about 24 hours to about seven days. The product of this reaction may be isolated, but is preferably hydrolyzed directly to a compound of formula I wherein $R^1$ and $R^2$ are hydrogen. This hydrolysis is conducted in 6N hydrochloride acid at a temperature of about 100° C. for a period of about 2 to about 24 hours, to produce a compound of formula I wherein $R^3$ is tetrazole.

The formula I compound wherein $R^3$ is a hydroxyisoxazole group are prepared as shown in Scheme III.

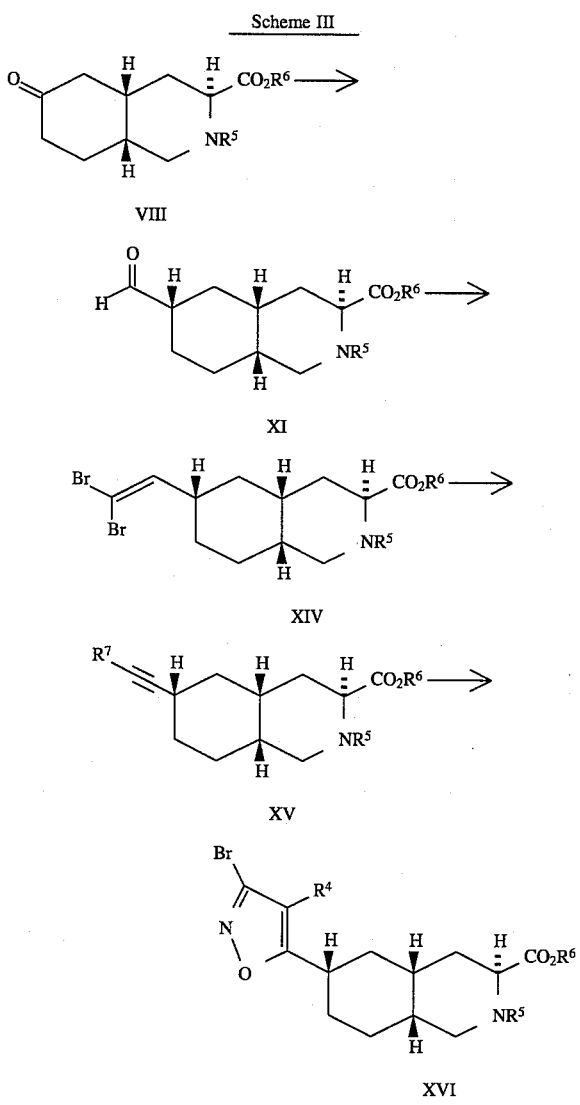

Scheme III

Generally, 6-keto intermediate VIII is converted to the 6-formyl intermediate XI as described above. This 6-formyl intermediate XI is converted to dibromoolefin intermediate XIV and then to ethynyl intermediate XV according to the procedure described by Corey and Fuchs. Corey and Fuchs, *Tetra. Lett.*, 36, 3769–3772 (1972). The ethynyl intermediate XV is modified using standard techniques and converted to a hydroxyisoxazole group to prepare the formula I compounds.

More specifically, 6-formyl intermediate XI is treated with a mixture of triphenylphosphine and carbontetrabromide to produce dibromoolefin intermediate XIV. The reaction is generally carried out in methylene chloride at a temperature of about 0° C. for a period of about 5 minutes to about 1 hour. Alternatively, a mixture of zinc dust, triphenylphosphine, and carbontetrabromide in methylene chloride is allowed to react at room temperature for about 24 to about 30 hours, and then treated with the 6-formyl intermediate. The second reaction is carried out at a temperature of about 20° C. to about 30° C. for a period of about 1 to about 2 hours.

Dibromoolefin intermediate XIV is then converted to ethynyl intermediate XV. Treatment of the dibromoolefin intermediate with about two equivalents of n-butyllithium produces the lithium acetylide, XV, wherein $R^7$ is lithium. This transformation is typically carried in a polar organic solvent, such as tetrahydrafuran, at a temperature of about –78° C. to about 25° C. The lithium acetylide is reacted with electrophiles, such as $C_1$–$C_4$ alkyl halides, phenyl halides, or N-halosuccinimides, to prepare the intermediate compounds wherein $R^7$ is a $R^4$ group as defined previously. In a typical example, the lithium acetylide is treated with iodomethane at a temperature of about –78° C. to about –60° C. to prepare intermediate XV wherein $R^7$ is methyl.

Acetylenic intermediate XV is then converted to a hydroxyisoxazole intermediate XVI. Intermediate XV is reacted with dibromoformaldoxime to produce a cycloadduct. This reaction is carried out at a temperature of about 15° C. to about 50° C., preferably at room temperature. A suitable solvent for this reaction is ethyl acetate. The cycloadduct, a 3-bromoisoxazole, is then treated with aqueous base to hydrolyze the bromo group. Suitable aqueous bases include sodium hydroxide and potassium hydroxide; potassium hydroxide is preferred. This reaction is carried out in a water miscible organic solvent, such as methanol. The reaction is preferably carried out at the reflux temperature of the solvent mixture.

The formula I compounds wherein $R^1$ is acyl are prepared by the reaction of a formula I compound wherein $R^1$ is hydrogen with an activated ester of the desired acyl group. The term activated ester means an ester which renders the carboxyl function of the acylating group reactive to coupling with the amino group of the decahydroisoquinoline ring. The preferred activated ester is the 2,4,5-trichlorophenyl ester. The reaction is carried out in a polar organic solvent, such as dimethylformamide or tetrahydrofuran, at a temperature of about 25° C. to 110° C. for a period of about 1 to about 5 hours. The reaction for the formation of acyl derivatives of the formula I compounds is preferably carried out at a temperature of about 30° C. to about 70° C. for a period of about 2 to about 4 hours.

The formula I compounds wherein $R^1$ is a $C_1$–$C_{10}$ alkyl or arylalkyl group are prepared using standard synthetic methods. One method for the synthesis of these compounds is the reaction of the aldehyde corresponding to the $C_1$–$C_{10}$ alkyl or arylalkyl group with a formula I compound wherein $R^1$ is hydrogen in the presence of a reducing agent. Suitable reducing agents include sodium cyanoborohydride and formic acid. This reaction is typically carried out in a polar organic solvent, such as methanol or ethyl acetate, at room temperature. The formula I compounds wherein $R^1$ is alkoxycarbonyl or aryloxycarbonyl are prepared using procedures similar to that described above for the synthesis of intermediate VI.

The formula I compounds wherein $R^2$ is $C_1$–$C_6$-alkyl, substituted alkyl, cycloalkyl, or arylalkyl are prepared from the corresponding compounds wherein $R^2$ is hydrogen. These compounds are generally prepared using standard synthetic methodologies. In a typical example, the formula I compound, wherein $R^1$ is hydrogen, is reacted with an aryl-alkyl halide, such as benzyl bromide, in the presence of a base to produce the arylalkyl ester derivative. Suitable bases for this transformation include tertiary amines, such as triethylamine, N,N-diisopropylethyl amine, N-methylmorpholine, pyridine, and collidine, and sodium carbonate. The reaction is typically run in an organic solvent, such as tetrahydrofuran, acetonitrile, and dimethylformamide. Alternatively, the formula I compound, wherein $R^1$ is hydrogen, can be reacted with a substituted alkyl, cycloalkyl, or arylalkyl alcohol in the presence of acid to produce the corresponding ester. Typically, this reaction is carried out with an excess of the alcohol in the presence of concentrated sulfuric acid.

The formula I compounds of the present invention are excitatory amino acid antagonists. In particular, these compounds are antagonists of the AMPA and NMDA subtypes of excitatory amino acid receptors. Therefore, another aspect of the present invention is a method of blocking the AMPA or NMDA excitatory amino acid receptors in mammals which comprises administering to a mammal requiring decreased excitatory amino acid neurotransmission a pharmaceutically-effective amount of a compound of formula I.

The term "pharmaceutically-effective amount" is used herein to represent an amount of the compound of the invention which is capable of blocking the AMPA or NMDA excitatory amino acid receptors. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular, or intranasal routes. Alternatively, the compounds may be administered by continuous infusion. A typical daily dose will contain from about 0.01 mg/kg to about 30 mg/kg of the active compound of this invention. Preferred daily doses will be about 0.05 mg/kg to about 24 mg/kg, more preferably about 0.1 to about 20 mg/kg.

A variety of physiological functions have been shown to be subject to influence by excessive or inappropriate stimulation of excitatory amino acid neurotransmission. The formula I compounds of the present invention are believed to have the ability to treat a variety of neurological disorders in mammals associated with this condition which include acute neurological disorders such as cerebral deficits subsequent to cardiac bypass surgery and grafting, stroke, cerebral ischemia, spinal cord trauma, head trauma, perinatal hypoxia, cardiac arrest and hypoglyemic neuronal damage. The formula I compounds are believed to have the ability to treat a variety of chronic neurological disorders such as Alzheimer's Disease, Huntington's Chorea, amyotrophic lateral sclerosis, AIDS-induced dementia, ocular damage and retinopathy, and idiopathic and drug-induced Parkinson's Disease. The present invention also provides methods for treating these disorders which comprise administering to a patient in need thereof an effective amount of a compound of formula I.

The formula I compounds of the present invention are also believed to have the ability to treat a variety of other neurological disorders in mammals that are associated with glutamate dysfunction including muscular spasms, convulsions, migraine headaches, urinary incontinence, psychosis, opiate tolerance and withdrawal, anxiety, emesis, brain edema, chronic pain, and tardive dyskinesia. The formula I compounds are also useful as analgesic agents. Therefore, the present invention also provides methods for treating these disorders which comprise administering to a patient in need thereof an effective amount of a compound of formula I.

Experiments were performed to demonstrate the inhibitory activity of the formula I compounds of this invention at the $\alpha$-amino-3-hydroxy-5-methylisoxazole-4-propionic acid (AMPA) and N-methyl-D-aspartate (NMDA) subtypes of excitatory amino acid receptors. The formula I compounds were tested for their ability to inhibit NMDA, AMPA, and kainic acid receptor binding to rat membranes in a radioligand binding assay using [$^3$H]CGS19755, [$^3$H]AMPA, and [$^3$H]KA. For all radioligand binding assays, male Sprague-Dawley rats were used. Displacement of the specific binding [$^3$H]CGS19755 (10 nM) to Triton-X-treated synaptosomal membranes of rat forebrain was used to determine NMDA receptor affinity. Non-specific binding was determined using 10 µM L-glutamate. Samples were incubated in an ice-bath for 30 minutes, and bound ligand was separated from the free ligand by rapid filtration through WHATMAN GF/B glass fiber filters. Murphy et al, *British J. Pharmacol.*, 95, 932–938 (1988). Kainate binding was performed using washed synaptosomal membranes from the rat forebrain as described by Simon et al. Simon et al, *J. Neurochem.*, 26, 141–147 (1976). Tritiated kainate (5 nM) was added to 50 mM Tris-HCl buffer (pH 7.4 at 4° C.) containing 200–300 µg/ml of tissue protein. Samples were incubated for 30 minutes in an ice-bath, then rapidly filtered using a Brandel cell harvester and WHATS GF/C filters. Filters were washed twice with 3 ml of cold buffer. Non-specific binding was determined using 100 µM non-labeled kainate. The binding of [$^3$H]AMPA (5 nM) was conducted with crude membranes of rat forebrain in the presence of 100 mM KSCN as described by Nielson et al. Nielson et al, *Eur. J. Med. Chem. Chem. Ther.*, 21, 433–437 (1986). Non-specific binding was determined with 10 µM non-labeled AHPA. The concentration of the formula I compound that inhibited 50% binding (IC$_{50}$, mean ± standard error, n=3) as calculated by linear regression of displacement data transformed to the Hill equation as described by Bennett. Bennett, Neurotransmitter Receptor Binding, 57–90 (1978). The results of the radioligand binding assays are shown in Table I.

TABLE I

Receptor Binding of Formula I Compounds

| Compound No. | Structure | IC$_{50}$ (µM)[a] | | |
|---|---|---|---|---|
| | | NMDA | AMPA | KA |
| 1[b] | (structure) | 1.56 ± 0.23 | 12.84 ± 0.27 | 31.84 ± 2.31 |

TABLE I-continued

Receptor Binding of Formula I Compounds

| Compound No. | Structure | IC$_{50}$ (μM)[a] | | |
|---|---|---|---|---|
| | | NMDA | AMPA | KA |
| 2[c] | (triazole-cyclohexyl-CH$_2$-CH(NH)-CO$_2$H structure) | 0.96[d] | 5.72 ± 0.89 | 21.0[d] |

[a] Mean ± standard error (n = 3), unless otherwise indicated.
[b] The compound was tested as a racemic mixture with the relative stereochemistry as shown.
[c] The compound was tested as a single enantiomer with the absolute stereochemistry as shown.
[d] The data is the result of a single experiment.

The depolarization of rat cortical wedges was used to test the selectivity and potency of the formula I compounds as AMPA and NTMDA antagonists using a technique similar to that described by Harrison and Simmonds. Harrison and Simmonds, *Bri. J. Pharmacol.*, 84, 381–391 (1984). Generally, 4-ml aliquots of NMDA (40 μM), AMPA (40 μM), and kainate (10 μM) were superfused (2 ml/min.) on the grey matter at intervals of 15–20 minutes until stable responses were attained. The tissue was then exposed for 15 minutes to various concentrations of the formula I compounds before retesting the agonists. The IC$_{50}$ values were calculated from linear regression of log dose-response curves, each point the mean of at least three observations on separate slices from more than one animal. The results of these tests are shown in Table II.

NMDA selectivity. This assay also distinguishes between agohist and antagonist activity. The formula I compounds, in particular compound 2, are shown to be AMPA and NMDA receptor antagonists (Table II).

The compounds of the present invention are preferably formulated prior to administration. Therefore, another aspect of the present invention is a pharmaceutical formulation comprising a compound of formula I and a pharmaceutically-acceptable carrier, diluent, or excipient.

The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper, or

TABLE II

Antagonism of Cortical Wedge Depolarization by Formula I Compounds

| Compound No. | Structure | IC$_{50}$ (μM)[a] | | |
|---|---|---|---|---|
| | | NMDA | AMPA | KA |
| 1[b] | (triazole-cyclohexyl-CH$_2$-CH(NH)-CO$_2$H structure) | 7.5 ± 0.7 | 40.9 ± 5.2 | >100 |
| 2[c] | (triazole-cyclohexyl-CH$_2$-CH(NH)-CO$_2$H structure) | 4.1 ± 0.3 | 13.2 ± 2.4 | >100 |

[a] Mean ± standard error (n = 3).
[b] The compound was tested as a racemic mixture with the relative stereochemistry as shown.
[c] The compound was tested as a single enantiomer with the absolute stereochemistry as shown.

The data shows that the formula I compounds possess selective affinity for the AMPA and the NMDA ionotropic glutamate receptors. The radioligand binding assay is the preferred assay for discriminating between AMPA and KA selectivity. The formula I compounds, in particular compound 2, displaced $^3$H-AMPA and [$^3$H]CGS19755 with IC$_{50}$ values less than 10 μM (Table I). The cortical wedge assay is the preferred assay for discriminating between AMPA and other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium sterate and mineral oil. The formulations can additionally include lubricating agents, wetting agents, emulsifying and suspending agents, preserving agents, sweetening agents, or flavoring agents. Compositions of the inventions may be formulated so as to provide quick, sustained, or delayed release of the active ingredient after administration to the patient by employing procedures well known in the art.

The compositions are preferably formulated in a unit dosage form, each dosage containing from about 5 to about 5000 mg, more preferably about 25 to about 3000 mg of the active ingredient. The most preferred unit dosage form contains about 100 to about 2000 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier. The following formulation examples are illustrative only and are not intended to limit the scope of the invention in any way.

Formulation 1
Hard gelatin capsules are prepared using the following ingredients:

|  | Quantity (mg/capsule) |
|---|---|
| 6-(1(2)H-Tetrazole-5-yl)-decahydroisoquinoline-3-carboxylic acid | 250 |
| Starch, dried | 200 |
| Magnesium stearate | 10 |
| Total | 400 mg |

The above ingredients are mixed and filled into hard gelatin capsules in 460 mg quantities.

Formulation 2
A tablet is prepared using the ingredients below:

|  | Quantity (mg/tablet) |
|---|---|
| 6-(1(2)H-Tetrazole-5-yl)decahydro-isoquinoline-3-carboxylic acid | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

|  | Weight % |
|---|---|
| 6-(3-Hydroxyisoxazol-5-yl)decahydro-isoquinoline-3-carboxylic acid | 0.25 |
| Ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| 6-(3-Hydroxyisoxazol-5-yl)decahydro-isoquinoline-3-carboxylic acid | 60 mg |
|---|---|
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| 6-(1(2)H-Tetrazole-5-yl)-decahydroisoquinoline-3-carboxylic acid | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 sieve, and filled into hard gelatin capsules in 200 mg quantities.

Formulation 6
Suppositories each containing 225 mg of active ingredient may be made as follows:

| 6-(3-Hydroxyisoxazol-5-yl)decahydro- | 225 mg |
|---|---|

-continued

Formulation 6
Suppositories each containing 225 mg of active ingredient may be made as follows:

| | |
|---|---|
| isoquinoline-3-carboxylic acid | |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| | |
|---|---|
| 6-(3-Hydroxyisoxazol-5-yl)decahydro-isoquinoline-3-carboxylic acid | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| | |
|---|---|
| 6-(1(2)H-Tetrazole-5-yl)-decahydroisoquinoline-3-carboxylic acid | 100 mg |
| Mannitol | 100 mg |
| 5N Sodium hydroxide | 200 μl |
| Purified water to total | 5 μl |

The following Examples further illustrate the compounds of the present invention and the methods for their synthesis. The Examples are not intended to be limiting to the scope of the invention in any respect, and should not be so construed. All experiments were run under a positive pressure of dry nitrogen. Tetrahydrofuran (THF) was distilled from sodium prior to use. All other solvents and reagents were used as obtained. Proton nuclear magnetic resonance ($^1$H NMR) spectra were obtained on a GE QE-300 spectrometer at 300.15 MHz or a Bruker AM-500 spectrometer at 500 MHz. Where indicated, a small amount of 40% aqueous KOD was added to aid solution of NMR samples run in $D_2O$. Chromatographic separation on a WATERS Prep 500 LC was generally carried out using a linear gradient of hexane to the solvent indicated in the text. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection [plates dipped in a ceric ammonium molybdate solution (75 g of ammonium molybdate and 4 g of cerium (IV) sulfate in 500 mL of 10% aqueous sulfuric acid) and then heated on a hot plate]. Flash chromatography was performed as described by Still, et al. Still, Kahn, and Mitra, *J. Org. Chem.*, 43, 2923 (1978). Elemental analyses for carbon, hydrogen, and nitrogen were determined on a Control Equipment Corporation 440 Elemental Analyzer. Melting points were determined in open glass capillaries on a Gallenkamp hot air bath melting point apparatus, and are uncorrected.

Preparation 1

6-Hydroxytetrahydroisoquinoline-3-carboxylic Acid
(V)

A slurry of d,l-m-tyrosine (1.91 kg) in dilute hydrochloric acid (76 ml of conc. HCl, 11.5 L of water) was heated to 55°–60° C., and treated with formaldehyde (1.18 L). Heating at 55°–70° C. was continued for 2 hours, then the reaction mixture was cooled to 3°–10° C. for 2 hours. The resulting mixture was filtered, and the filtrate washed with deionized water and acetone. The filter cake was dried in a vacuum oven at 55°–60° C. to give 1.88 kg of the title compound.

$^1$H NMR ($D_2O$/KOD): δ 6.75 (d, 1H), 6.35 (d, ! H), 6.30 (s, 1H), 3.77 (d, 1H), 3.69 (d, 1H), 3.26 (dd, 1H), 2.79 (dd, 1H), 2.60 (dd, 1H).

Analysis calculated for $C_{10}H_{11}NO_3 \cdot 0.85\ H_2O$: C, 57.60; H, 6.13; N 6.71. Found: C, 57.70; H, 6.43; N, 6.69.

Preparation 2

Ethyl
6-Hydroxy-2-methoxycarbonyltetrahydroisoquinoline-3
-carboxylate (VI)

To a mixture of the compound from Preparation 1 (91.2 g) in ethanol (455 ml) was added concentrated sulfuric acid (27.5 ml) over a period of two minutes. After the initial exothermic reaction, the solution was heated at reflux for 16 hours. The resulting solution was cooled in an ice water bath, and a solution of potassium carbonate (130.5 g) in water (130.5 ml) was added. Methyl chloroformate (36.5 ml) was added to this solution at a rate such that the pH was greater than 6.9 and the temperature was less than 14° C. After an additional two hours, the reaction mixture was partitioned between ethyl acetate (250 ml) and water (500 ml). The layers were separated and the aqueous layer extracted with two portions of ethyl acetate (100 ml each). The organic layers were combined and concentrated in vacuo to give a solid residue. The residue was crystallized by dissolving in refluxing ethanol (180 ml), diluting the ethanol solution with water (360 ml), and stirring the resulting mixture at 4° C. for 24 hours. The crystalline solid was collected by filtration and dried in a vacuum oven (40° C., 23 hours) to give 93.9 g of the title compound.

$^1$H NMR (CDCl$_3$): δ 6.95 (m, 1H), 6.67 (d, 1H), 6.61 (s, 1H), 5.76 (s, 1H), 5.06 and 4.85 (m, 1H), 4.65 (dd, 1H), 4.48 (d, 1h), 4.05 (m, 2H), 3.78 and 3.73 (s, 3H), 3.11 (m, 2H, 1.11 (t, 3H) (doubling due to amide rotamers).

Analysis calculated for $C_{14}H_{17}NO_5$: C, 60.21; H, 6.14; N, 5.02. Found: C, 60.49; H, 6.24; N, 4.98.

Preparation 3

Ethyl
2-Methoxycarbonyl-6-oxodecahydroisoquinoline-3
-carboxylate (VIII)

Alternative 1.

A. Preparation of Ethyl 6-Hydroxy-2-methoxycarbonyldecahydroisoquinoline-3-carboxylate (VII)

To a mixture of 3% rhodium on alumina (6.9 g) in ethyl acetate (350 ml) was added the compound from Preparation 2 (69.03 g). After sealing the vessel, the nitrogen atmosphere was replaced with hydrogen. The reaction was heated to 85° C. at a pressure of 100 psi for 23 hours. An additional portion of rhodium on alumina (1.4 g) was added and the heating resumed at elevated pressure for an additional two hours. The catalyst was removed by filtration, and the filtrate containing the title compound was used in the next step.

B. Preparation of Ethyl 2-Methoxycarbonyl-6-oxodecahydroisoquinoline-3-carboxylate (VIII)

To a solution of ruthenium(III) chloride (69 mg) in water (9.8 ml) was added the filtrate from Preparation 3A. The resulting two-phase mixture was cooled in an ice-water bath and treated with a solution of periodic acid (69 g) in water (26.9 ml). The periodic acid solution was added at a rate such that the temperature of the reaction mixture was less than 7.8° C. After the addition of the periodic acid, the ice bath was removed and the reaction mixture was allowed to warm to room temperature. After 1¼ hours, the aqueous phase was removed and the organic phase washed with two portions of water (50 ml each). The organic phase was concentrated to dryness in vacuo to give 67.7 g of the title compound as an oil.

Alternative 2.

Preparation of Ethyl 6-Hydroxy-2-methoxycarbonyldecahydroisoquinoline-3-carboxylate (VII) and Ethyl 2-Methoxycarbonyl-6-oxodecahydroisoquinoline-3-carboxylate (VIII)

A mixture of 3% rhodium on carbon 1.0 kg) and the compound prepared as described in Preparation 2 (13.2 kg) in ethyl acetate (67 liters) was hydrogenated at a hydrogen pressure of 100 psi at about 85° C. After 23 hours, the reaction mixture was cooled to room temperature and the catalyst removed by filtration. The catalyst cake was washed with additional ethyl acetate (10 liters), and the ethyl acetate filtrates combined.

A sample of the ethyl acetate solution from the preceding paragraph was concentrated in vacuo to give 3.295 g of colorless oil, which was a mixture of C-6 ketone and C-6 alcohols. This mixture was separated by silica-gel flash chromatography, eluting with a linear gradient of methylene chloride to methylene chloride/ethyl acetate (9:1) followed by ethyl acetate, to give two products. The fractions containing the first product were combined and concentrated in vacuo to give 1.18 g of compound VIII. The fractions containing the second product were combined and concentrated in vacuo to give 1.36 g of compound VII.

Preparation 4

(3S, 4aS, 8aR)-(−) Ethyl 2-Methoxycarbonyl-6-oxodecahydroisoquinoline-3-carboxylate ((−)-VIIIb)

A. Preparation of 2-Methoxycarbonyl-6-oxodecahydroisoquinoline-3-carboxylic Acid The compound from Preparation 3B (1.913 kg) was added to a 21% sodium ethoxide solution (509 g) in ethanol (8 L). The resulting solution was heated to reflux for a period of six hours, and then allowed to cool to room temperature over a period of 24 hours. This solution was treated with 5N sodium hydroxide solution (2.4 L) and allowed to remain at a temperature of about 25° C. to about 40° C. for a period of two hours. The reaction mixture was concentrated in vacuo to remove the ethanol. The residue was extracted with two portions of t-butylmethyl ether (5 L each), and the pH of the aqueous phase was adjusted to about 1.5 to about 2.5 by adding concentrated hydrochloric acid (1.7 L). The title compound was extracted from the aqueous solution with ethyl acetate (4×3 L). The combined ethyl acetate extracts were treated with FLORISIL (960 g) and sodium sulfate (960 g). The ethyl acetate filtrate containing the title compound was used in the next step without further purification.

B. Preparation of (3S, 4aS, 8aR)-(−)-2-Methoxycarbonyl-6-oxodecahydroisoquinoline-3-carboxylate α-methylbenzylamine salt To the ethyl acetate filtrate from Preparation 4A was added R-(+)-α-methylbenzylamine at a temperature of about 25° C. to about 30° C. over a period of one hour. The resultant slurry was allowed to remain at room temperature for a period of 24 hours, and then the precipitate was collected by filtration. The solid material was rinsed with several portions of ethyl acetate until the rinse was colorless. The filter cake was dried in a vacuum oven at a temperature of about 45°–50° C. This material was reslurried in 10 volumes of ethyl acetate at a temperature of about 45° C. to about 50° C. for about four hours, the solution was allowed to cool to ambient temperature, and the solid material removed by filtration. The solids were dried in vacuo at about 45° C. to about 50° C. to give 1.092 kg of the title compound.

$[\alpha]_D = -57.0°$ (c=1, $H_2O$).

Analysis calculated for $C_{20}H_{28}N_2O_5$: C, 63.81; H, 7.50; N, 7.44. Found: C, 63.87; H, 7.33; N, 7.33.

C. Preparation of (3S, 4aS, 8aR)-(−) Ethyl 2-Methoxycarbonyl-6-oxodecahydroisoquinoline-3-carboxylate ((−)-VIIIb)

A mixture of the compound from Preparation 4B (50 g) and acetonitrile (250 ml), was treated with triethylamine (26.8 g) and ethyl bromide (73 g). The resulting mixture was heated to reflux causing dissolution of the reactants. After about one to about two hours, the reaction was allowed to cool to room temperature and concentrated in vacuo. The residue was treated with ethyl acetate (250 ml). The resulting mixture was filtered and the solids rinsed with additional ethyl acetate. The filtrate was extracted with 3N hydrochloric acid, dried over $MgSO_4$, filtered, and concentrated in vacuo to give 34.9 g of the title compound.

$[\alpha]_D = -51.3°$ (c=1, $CH_2Cl_2$)

Analysis calculated for $C_{14}H_{21}NO_5$: C, 59.35; H, 7.47; N, 4.94. Found: C, 59.11; H, 7.20; N, 4.90.

D. Preparation of (3R4aR8aS)-(+) Ethyl 2-Methoxycarbonyl-6-oxodecahydroisoquinoline-3-carboxylate ((+)-VIIIb)

The title compound was prepared from the racemic mixture from Preparation 4A using the procedures described in Preparation 4B and 4C with S-α-methylbenzylamine.

Preparation 5

(3SR, 4aSR, 8aRS) Ethyl 2-Methoxycarbonyl-6-oxodecahydroisoquinoline-3-carboxylate ((±)-VIIIb)

A. Preparation of Ethyl 6-Hydroxy-2-methoxycarbonyldecahydroisoquinoline-3-carboxylate A mixture of the compound from Preparation 2 (158.9 g) and 5% ruthenium on alumina (80 g) in ethanol (1760 ml) was hydrogenated at a pressure of 2000 psi. After 16 hours at about 180° C., the cooled reaction mixture was filtered through CELITE, and the filtrate concentrated in vacuo. The residue was diluted with ethyl acetate. This mixture was filtered through CELITE, and concentrated in vacuo to give 156.7 g of the title compound.

B. Preparation of Ethyl 2-Methoxycarbonyl-6-oxodecahydroisoquinoline-3-carboxylate (VIII)

A solution of the compound from Preparation 5A (156.7 g) in methylene chloride (300 ml) was added to a mixture of pyridinium chlorochromate (260.5 g) and powdered 4 Å molecular sieves in methylene chloride (1400 ml), which was allowed to stir one hour prior to the addition of the alcohol. After two hours, the reaction mixture was diluted with ether and filtered through a layer each of CELITE and silica gel. The solids were washed with ether, and the combined ether solutions concentrated in vacuo. The residue was dissolved in ether, filtered through CELITE and silica gel, and the filtrate concentrated in vacuo to give 128.8 g of a mixture of VIIIa and VIIIb (VIIIa:VIIIb =78:22).

C. Preparation of (3SR, 4aSR, 8aRS)-(±) Ethyl 2-Methoxycarbonyl-6-oxodecahydroisoquinoline-3-carboxylate (VIIIb)

A solution of the mixture from Preparation 5B (128.8 g) in ethanol (1000 ml) was treated with a solution of sodium hydride (1.82 g) in ethanol (100 ml), and the resulting mixture heated to reflux. After 1½ hours, the mixture was allowed to cool to room temperature and concentrated in vacuo. The residue was dissolved in methylene chloride/ether (1:1), and washed with 10% aqueous sodium bisulfate. The aqueous phase was extracted with ether, the organic phases combined, dried over magnesium sulfate, filtered, and concentrated in vacuo. The residue was purified by silica-gel chromatography on a WATERS PREP 500 LC, eluting with a linear gradient of hexane to 25% ethyl acetate/hexane, to give 106.9 g of a mixture of VIIIa and VIIIb (vIIIa:vIIIb=13:87). Recrystallization of this mixture from ether gave 67.0 g of the title compound. Melting point 78°–79° C.

$^1$H NMR (DMSO) δ: 4.76 (d, 1H), 4,124 (q, 2H), 3.80 (d, 1H), 3.61 (s, 3H), 3.21 (bd, 1H), 2.65 (dd, 1H), 2.43 (dt, 1H), 2.19 (m, 1H), 2.14 (m, 2H), 1.98 (ddd, 1H), 1.85 (m, 1H), 1.75 (m, 1H), 1.65 (dt, 1H), 1.20 (t, 3H).

Analysis calculated for $C_{14}H_{21}NO_5$: C, 59.35; H, 7.47; N, 4.94. Found: C, 59.62; H, 7.61; N, 4.97.

EXAMPLE 1

(3SR, 4aRS, 6SR, 8aRS)-6-(1(2)H-Tetrazole-5-yl)decahydroisoquinoline-3-carboxylic Acid

A. Preparation of Ethyl 6-Methylidine-2-methoxycarbonyldecahydroisoquinoline-3-carboxylate Methyltriphenylphosphonium bromide (76.3 g) was added to tetrahydrofuran (800 ml). This mixture was stirred at room temperature for 15 minutes, then filtered. The solid was dried in vacuo at about 50° C. for 30 minutes. The residue was suspended in tetrahydrofuran (220 ml) and the resulting mixture cooled to 0° C. The cold mixture was treated with a 1M solution of sodium bis(trimethylsilyl)amide in tetrahydrofuran (213.6 ml). After 15 minutes, the resulting solution was added to a cold (0° C.) solution of the racemic compound from Preparation 5C (43.23 g) in tetrahydrofuran (320 ml) until a pale yellow color persisted. The reaction mixture was treated with water (250 ml) and ether (500 ml), and the phases separated. The organic phase was extracted with water (10 ml), and the aqueous phase extracted with ether (2 times). The organic phases were combined, dried, and concentrated in vacuo. The residue was suspended in 25% ethyl acetate/hexane and the resulting mixture stirred at room temperature. After one hour, the mixture was filtered and the solids rinsed with 25% ethyl acetate/hexane. The filtrate was concentrated in vacuo. The residue was purified by silica-gel flash chromatography, eluting with 25% ethyl acetate/hexane, to give 40.67 g of the title compound.

B. Preparation of (3SR, 4aRS, 6SR, 8aRS) Ethyl 6-Hydroxymethyl-2-methoxycarbonyldecahydroisoquinoline-3-carboxylate A cold (0° C.) solution of the compound from Example 1A (40.67 g) in tetrahydrofuran (285 ml) was treated with a 10M solution of borane-methyl sulfide (9.7 ml). After two hours at 0° C., the reaction was allowed to warm to room temperature. After an additional 2½ hours, the reaction mixture was cooled to 0° C. and treated with ethanol (25 ml), 3N sodium hydroxide (200 ml), and 30% hydrogen peroxide (200 ml). After 30 minutes at 0° C., the reaction mixture was allowed to warm to room temperature. After an additional two hours at room temperature, this mixture was extracted with ether (3 times). The combined organic extracts were dried over magnesium sulfate, filtered, and concentrated in vacuo. The residue was purified by silica-gel chromatography on a WATERS PREP 500 LC, eluting with a gradient of hexane to 60% ethyl acetate/hexane, to give 40.36 g of the title compound.

C. Preparation of (3SR, 4aRS, 6SR, 8aRS) Ethyl 6-Formyl-2-methoxycarbonyldecahydroisoquinoline-3-carboxylate A solution of dimethylsulfoxide (22.5 ml) in methylene chloride (250 ml) was cooled to −78° C. and treated with oxalyl chloride (13.3 ml). After five minutes, this cold solution was treated with a solution of the compound from Example 1B (38.0 g) in methylene chloride (150 ml). After an additional 15 minutes, this mixture was treated with triethylamine (88.5 ml). After an additional 45 minutes at −78° C., the reaction mixture was allowed to warm to room temperature and treated with 10% sodium bisulfate (1000 ml) and ether (750 ml). The phases were separated and the aqueous extracted with ether (2 times). The organic phases were combined, dried over magnesium sulfate, filtered, and concentrated in vacuo. The residue was used in the next step without further purification.

D. Preparation of (3SR, 4aRS, 6RS, 8aRS) Ethyl 6-cyano-2-methoxycarbonyldecahydroisoquinoline-3-carboxylate A solution of the compound from example 1C (37.8 g) in methylene chloride (570 ml), methanol (165 ml) and pyridine (20.5 ml) was treated at room temperature with hydoxylamine hydrochloride (8.83 g). After 30 minutes at room temperature, the reaction mixture was concentrated in vacuo, then additional methylene chloride (300 ml) was added and the mixture again concentrated in vacuo. The residue was dissolved in methylene chloride (870 ml) and pyridine (20.5 ml), cooled to 0° C. and treated drop-wise with phenylphosphonic dichloride (36.0 ml). After stirring overnight at room temperature, the reaction mixture was quenched with saturated aqueous sodium bicarbonate (750 ml), then ether (1000 ml) was added, the phases separated and the organic phase washed with 10% sodium bisulfate (750 ml). The organic phase was dried over magnesium sulfate, filtered, and concentrated in vacuo. The residue was purified by silica-gel chromatography on a WATERS PREP 2000 LC, loading in 25% ethyl acetate/toluene and eluting with a gradient of 5% ethyl acetate/hexane to 35% ethyl acetate/hexane, to give 31.6 g of the title compound.

E. Preparation of (3SR, 4aRS, 6RS, 8aRS)-6-[2-(1(2)H-Tetrazole-5-yl)ethyl]decahydroisoquinoline-3-carboxylic Acid The compound from Example 1D (31.6 g) and tributyltin azide (79.2 g) in toluene (30 ml) was heated to 80° C. After 7 days, the mixture was treated with 6N hydrochloric acid (250 ml) and heated to 100° C. After heating about 18 hours, the mixture was allowed to cool to room temperature. This mixture was extracted six times with ether (200 ml), and the aqueous phase concentrated in vacuo. The residue was purified by ion-exchange chromatography on DOWEX 50X8, eluting with 10% pyridine/water. The fractions containing the title compound were combined and concentrated in vacuo. The residue was diluted with water and concentrated in vacuo. This procedure was repeated. The residue was suspended in 150 ml water, cooled to 0° C. for 4 hours, then filtered and the solids washed with acetone and ether. The solid material was dried in vacuo at 60° C. for about 18 hours, to give 16.4 g of the title compound. Melting point 283° C.

Analysis calculated for $C_{11}H_{17}N_5O_2 \cdot 0.55H_2O$: C, 50.58; H, 6.98; N, 26.81. Found: C, 50.57; H, 6.75; N, 26.57.

EXAMPLE 2

(3S, 4aR, 6S, 8aR)-6-(1(2)H-Tetrazole-5-yl)decahydroisoquinoline-3-carboxylic Acid A. Preparation of (3S, 4aR, 8aR) Ethyl 6-Methylidine-2-methoxycarbonyldecahydroisoquinoline-3-carboxylate The reaction of methyltriphenylphosphonium bromide (17.6 g), a 1 M solution of sodium bis(trimethylsilyl)amide in tetrahydrofuran (49 ml), and (3S, 4aS, 8aR)-(−) ethyl 2-methoxycarbonyl-6-oxodecahydroisoquinoline-3-carboxylate (10.0 g) as described in Example 1A produced the crude title compound. This material was purified by silica-gel flash chromatography, eluting with 25% ethyl acetate/hexane, to give 9.25 g of the title compound.

B. Preparation of (3S, 4aR, 6S, 8aR) Ethyl 6-Hydroxymethyl-2-methoxycarbonyldecahydroisoquinoline-3-carboxylate A cold (0° C.) solution of the compound from Example 2A (9.25 g) in tetrahydrofuran (65 ml) was treated with a 10M solution of borane-methyl sulfide (2.2 ml). After three hours, the reaction solution was treated with ethanol (7.5 ml), then 3N sodium hydroxide (22 ml), then 30% hydrogen peroxide (22 ml). After 1 hour at 0° C., this mixture was extracted with ether (3 times). The organic phases were combined, dried over magnesium sulfate, filtered, and concentrated in vacuo. The residue was purified by silica-gel chromatography on a WATERS PREP 2000 LC, eluting with a gradient of hexane to 60% ethyl acetate/hexane, to give 7.53 g of the title compound.

C. Preparation of (3S, 4aR, 6S, 8aR) Ethyl 6-Formyl-2-methoxycarbonytdecahydroisoquinoline-3-carboxylate A solution of dimethylsulfoxide (1.2 ml) in methylene chloride (14 ml) was cooled to −78° C. and treated with oxalyl chloride (0.7 ml). After five minutes, this cold solution was treated with a solution of the compound from Example 2B (2.00 g) in methylene chloride (6 ml). After an additional 15 minutes, this mixture was treated with triethylamine (4.7 ml). After an additional 45 minutes at −78° C., the reaction mixture was allowed to warm to room temperature and treated with 10% sodium bisulfate (50 ml) and ether (50 ml). The phases were separated and the aqueous extracted with ether (2 times). The organic phases were combined, dried over magnesium sulfate, filtered, and concentrated in vacuo. The residue was used in the next step without further purification.

D. Preparation of (3S, 4aR, 6S, 8aR) Ethyl 6-cyano-2-methoxycarbonyldecahydroisoquinoline-3-carboxylate A solution of the compound from example 2C (2.00 g) in methylene chloride (30 ml), methanol (9 ml) and pyridine (1.1 ml) was treated at room temperature with hydoxylamine hydrochloride (0.46 g). After 30 minutes at room temperature, the reaction mixture was concentrated in vacuo, then additional methylene chloride (30 ml) was added and the mixture again concentrated in vacuo. The residue was dissolved in methylene chloride (43 ml) and pyridine (1.1 ml), cooled to 0° C. and treated dropwise with phenylphosphonic dichloride (1.9 ml). After stirring overnight at room temperature, the reaction mixture was quenched with saturated aqueous sodium bicarbonate (50 ml), then ether (75 ml) was added, the phases separated and the organic phase washed with 10% sodium bisulfate (50 ml). The organic phase was dried over magnesium sulfate, filtered, and concentrated in vacuo. This material was purified by silica-gel flash chromatography, eluting with 35% ethyl acetate/hexane, to give 1.68 g of the title compound.

E. Preparation of (3S, 4aR, 6S, 8aR)-6-[2-(1(2)H-Tetrazole-5-yl)ethyl]decahydroisoquinoline-3-carboxylic Acid The compound from Example 2D (1.68 g) and tributyltin azide (3.68 g) was heated to 80° C. After 7 days, the mixture was treated with 6N hydrochloric acid (50 ml) and heated to 100° C. After heating about 18 hours, the mixture was allowed to cool to room temperature. This mixture was extracted six times with ether (20 ml), and the aqueous phase concentrated in vacuo. The residue was purified by ion-exchange chromatography on DOWEX 50X8, eluting with 10% pyridine/water. The fractions containing the title compound were combined and concentrated in vacuo. The residue was diluted with water and concentrated in vacuo. This procedure was repeated. The residue was treated with acetone, then heated to reflux for one hour. The cooled mixture was filtered and the solid material washed with acetone and ether, then dried in vacuo for about 18 hours at 60° C. to give 1.12 g of the title compound. Melting point 244°–247° C.

$[\alpha]_D = -22.8°$ (c=1, 1N HCl)

Analysis calculated for $C_{11}H_{17}N_5O_2 \cdot 1.25H_2O$: C, 48.25; 7.18; N, 25.58. Found: C, 48.16; H, 6.75; N, 25.83.

We claim:

1. A method of treating a neurological disorder in a patient, which comprises administering to a patient in need thereof, an effective amount of a compound of the formula

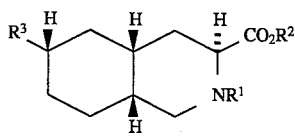

wherein:

$R^1$ is hydrogen, $C_1$–$C_{10}$ alkyl, arylalkyl, alkoxycarbonyl, aryloxycarbonyl, or acyl;

$R^2$ is hydrogen, $C_1$–$C_6$ alkyl, substituted alkyl, cycloalkyl, or arylalkyl;

$R^3$ is a group of the formula

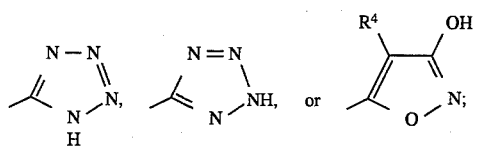

$R^4$ is hydrogen, $C_1$–$C_4$ alkyl, $CF_3$, phenyl, bromo, iodo, or chloro;

or a pharmaceutically acceptable salt thereof.

2. The method of claim 1 wherein said neurological disorder is cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug-induced Parkinson's Disease, anxiety, emesis, brain edema, chronic pain, or tardive dyskinesia.

3. The method of claim 1 wherein said neurological disorder is cerebral deficits subsequent to cardiac bypass surgery and grafting, stroke, cerebral ischemia, spinal cord trauma, head trauma, cardiac arrest, Alzheimer's Disease, idiopathic and drug-induced Parkinson's Disease, AIDS-induced dementia, convulsions, chronic pain, psychosis, emesis, muscular spasms, amyotrophic lateral sclerosis, or ocular damage and retinopathy.

4. The method of claim 1 wherein said neurological disorder is cerebral deficits subsequent to cardiac bypass surgery and grafting, stroke, cerebral ischemia, head trauma, spinal cord trauma, cardiac arrest, ocular damage and retinopathy, Alzheimer's Disease, idiopathic and drug-induced Parkinson's Disease, AIDS-induced dementia, convulsions, or chronic pain.

5. The method of claim 1 wherein said neurological disorder is cerebral deficits subsequent to cardiac bypass surgery and grafting, stroke, cerebral ischemia, head trauma, spinal cord trauma, cardiac arrest, or ocular damage and retinopathy.

6. A method of treating a neurological disorder in a patient, which comprises administering to a patient in need thereof, an effective amount of a compound of the formula

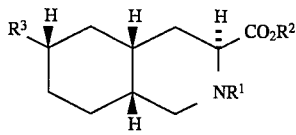

wherein:

$R^1$ is hydrogen;

$R^2$ is hydrogen;

$R^3$ is a group of the formula

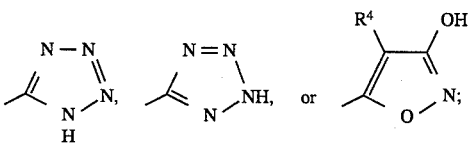

and $R^4$ is hydrogen, $C_1$–$C_4$ alkyl, $CF_3$ or phenyl;

or a pharmaceutically acceptable salt thereof.

7. The method of claim 6 wherein said neurological disorder is cerebral deficits subsequent to cardiac bypass surgery and grafting, stroke, cerbral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug-induced Parkinson's Disease, anxiety, emesis, brain edema, chronic pain, or tardive dyskinesia.

8. The method of claim 6 wherein said neurological disorder is cerebral deficits subsequent to cardiac bypass surgery and grafting, stroke, cerebral ischemia, spinal cord trauma, head trauma, cardiac arrest, Alzheimer's Disease, idiopathic and drug-induced Parkinson's Disease, AIDS-induced dementia, convulsions, chronic pain, psychosis, emesis, muscular spasms, amyotrophic lateral sclerosis, or ocular damage and retinopathy.

9. The method of claim 1 wherein said neurological disorder is cerebral deficits subsequent to cardiac bypass surgery and grafting, stroke, cerebral ischemia, head trauma, spinal cord trauma, cardiac arrest, ocular damage and retinopathy, Alzheimer's Disease, idiopathic and drug-induced Parkinson's Disease, AIDS-induced dementia, convulsions, or chronic pain.

10. The method of claim 6 wherein said neurological disorder is cerebral deficits subsequent to cardiac bypass surgery and grafting, stroke, cerebral ischemia, head trauma, spinal cord trauma, cardiac arrest, or ocular damage and retinopathy.

11. A method of producing analgesia in mammals which comprises administering to a mammal an effective amount of a compound of the formula

31

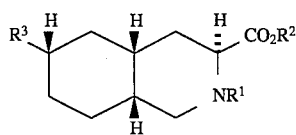

wherein:
R¹ is hydrogen, $C_1$–$C_{10}$ alkyl, arylalkyl, alkoxycarbonyl, aryloxycarbonyl, or acyl;
R² is hydrogen, $C_1$–$C_6$ alkyl, substituted alkyl, cycloalkyl, or arylalkyl;
R³ is a group of the formula

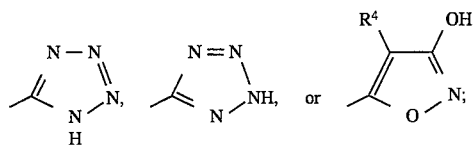

R⁴ is hydrogen, $C_1$–$C_4$ alkyl, $CF_3$, phenyl, bromo, iodo, or chloro;
or a pharmaceutically acceptable salt thereof.

12. A method of producing analgesia in mammals which comprises administering to a mammal an effective amount of a compound of the formula

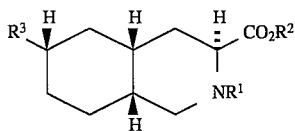

wherein:
R¹ is hydrogen;
R² is hydrogen;
R³ is a group of the formula

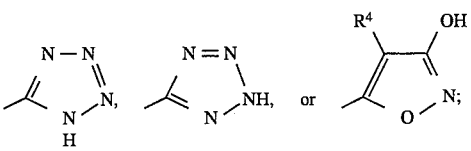

and R⁴ is hydrogen, $C_1$–$C_4$ alkyl, $CF_3$ or phenyl;
or a pharmaceutically acceptable salt thereof.

* * * * *

UNITED STATES PATENT AND TRADEMARK OFFICE
CERTIFICATE OF CORRECTION

PATENT NO.    : 5,527,810
DATED         : June 18, 1996
INVENTOR(S)   : Paul L. Ornstein It is certified that error appears in the above-indentified patent and that said Letters Patent is hereby corrected as shown below:

Column 30, line 50, "claim 1" should read --claim 6 --

Signed and Sealed this

Twenty-seventh Day of May, 1997

Attest:

BRUCE LEHMAN

Attesting Officer            Commissioner of Patents and Trademarks